United States Patent [19]

Engle et al.

[11] 4,359,904
[45] Nov. 23, 1982

[54] METHOD AND MEANS FOR ELIMINATING FOUNTAIN EFFECT IN AN ULTRASOUND SYSTEM DISPLAY

[75] Inventors: Gary L. Engle, Fair Oaks; Robert W. Cribbs, Placerville, both of Calif.

[73] Assignee: General Electric Company, Rancho Cordova, Calif.

[21] Appl. No.: 203,660

[22] Filed: Nov. 3, 1980

[51] Int. Cl.³ .............................................. G01N 29/00
[52] U.S. Cl. ...................................... 73/620; 128/660; 358/112
[58] Field of Search ..................... 73/620, 618, 607; 367/7; 358/112; 128/660

[56] References Cited

U.S. PATENT DOCUMENTS

| | | | |
|---|---|---|---|
| 4,172,386 | 10/1979 | Cribbs et al. | 73/618 |
| 4,204,433 | 5/1980 | Cribbs et al. | 73/620 |
| 4,206,654 | 6/1980 | Keller et al. | 73/620 |

*Primary Examiner*—Stephen A. Kreitman
*Attorney, Agent, or Firm*—Flehr, Hohbach, Test, Albritton & Herbert

[57] ABSTRACT

Pixel data is selectively updated in an ultrasound scanning system in which the monitor display includes a plurality of addressable pixels. A random access memory holds the intensity values for the display pixels, and the memory is updated in response to rescanning of a patient. Updating is inhibited for a pixel of a vector when the preceding vector included the same pixel. Spurious display effects are thereby minimized.

11 Claims, 6 Drawing Figures

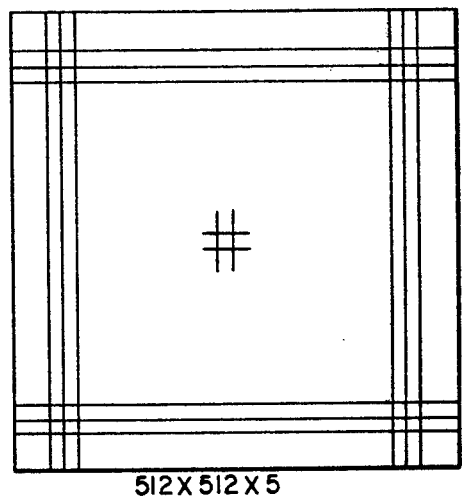
FIG.—2
512 X 512 X 5
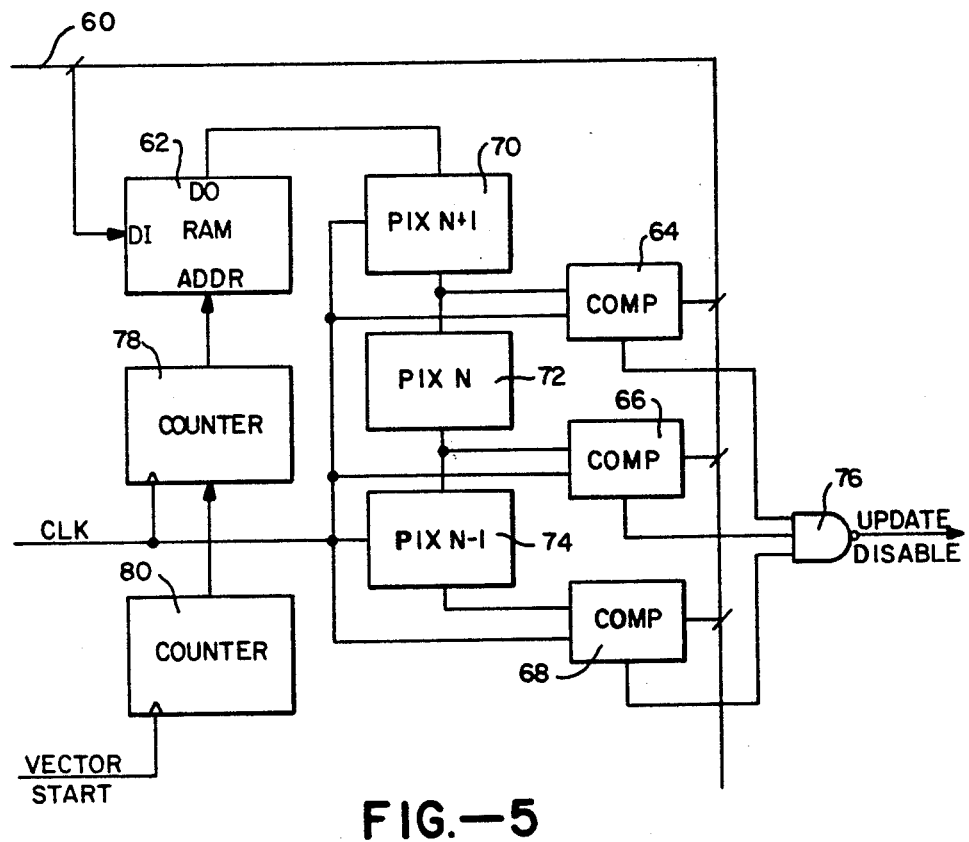
FIG.—5

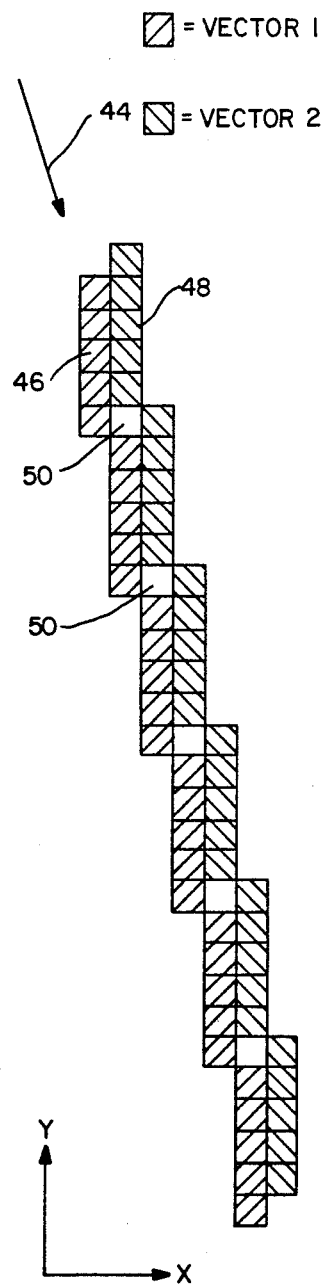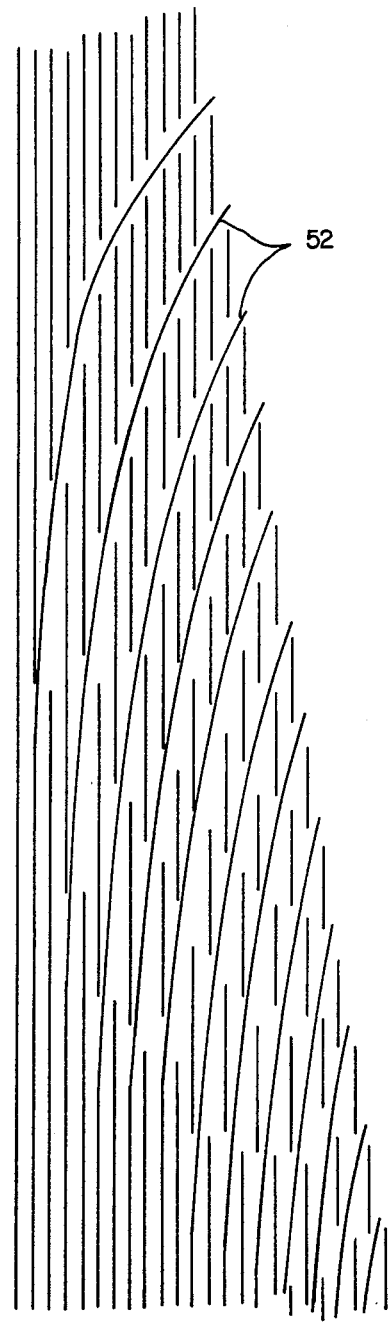
FIG.—3   FIG.—4

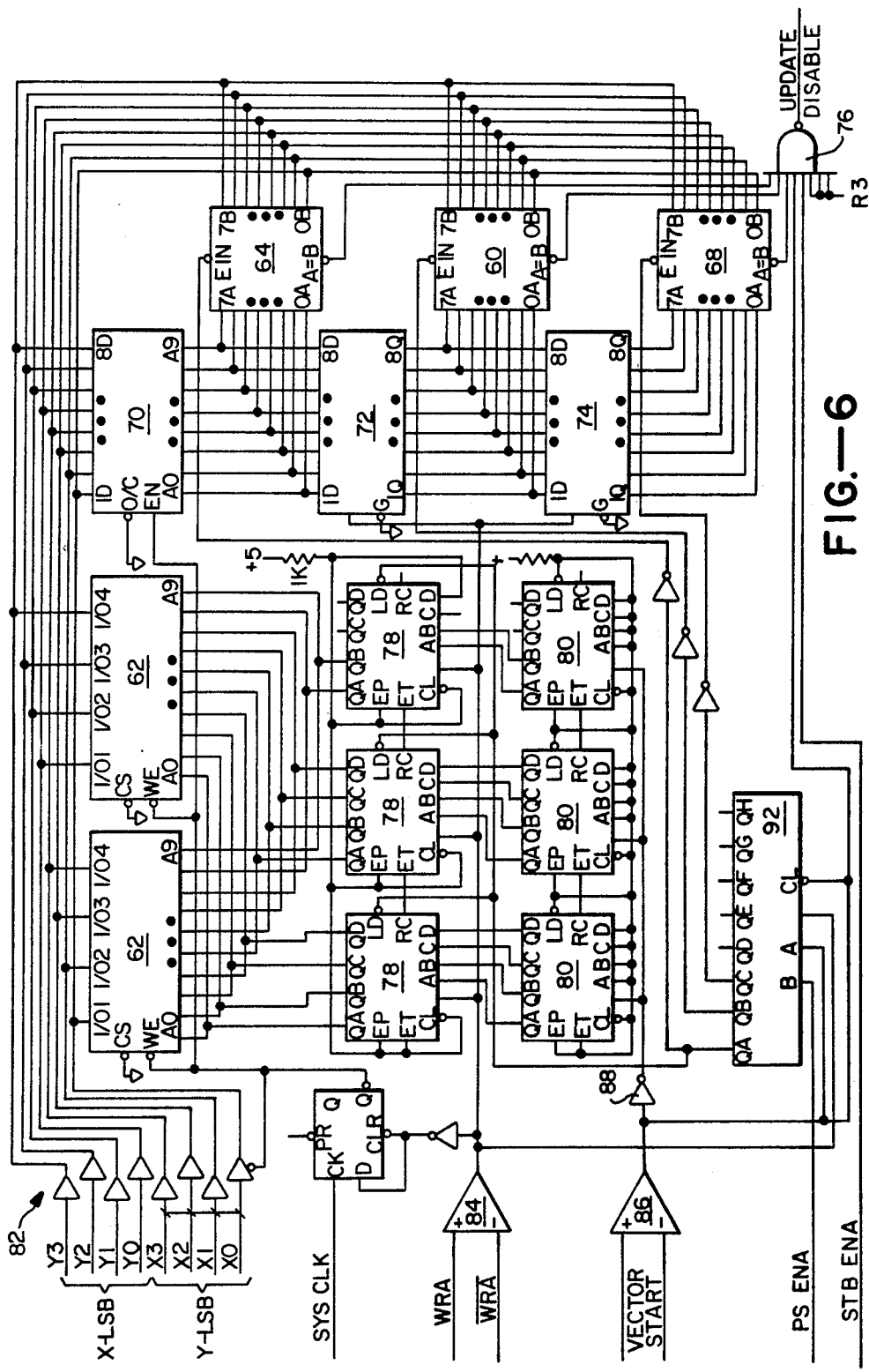
FIG.—6

METHOD AND MEANS FOR ELIMINATING FOUNTAIN EFFECT IN AN ULTRASOUND SYSTEM DISPLAY

This invention relates generally to ultrasonic scanners such as used for medical diagnostic purposes, and more particularly the invention relates to the storing and updating video data for display in such apparatus.

Ultrasonic diagnostic systems are known and commercially available for medical diagnostic purposes. See for example U.S. Pat. No. 4,172,386 for "Video A Trace Display System for Ultrasonic Diagnostic System" and U.S. Pat. No. 4,204,433 for "Computerized Ultrasonic Scanner With Technique Select". The Datason ultrasound system for General Electric provides both real time and static images on television display.

Briefly, such systems utilize sound transducers to transmit ultrasonic (e.g. on the order of several megahertz) waves into a patient and to receive echo signals. The transducer is attached to a plurality of hinged arms for movement in a single plane, and potentiometers associated with the hinged arms produce signals which identify the transducer's position. The echo signals are applied to a time gain compensated amplifier to adjust the echo signals for attenuation in passing through the patient. The adjusted signal is then passed through analog to digital conversion and video processing circuitry and thence to scan converter circuitry for formatting for display. The display comprises a plurality of illuminated spots or pixels in horizontal rows and vertical columns with each pixels having a brightness level in response to the input signal. Conventionally, the brightness is defined by a 32 level Gray scale, hence the pixel brightness level requires a 5 bit digital code.

The pixel data stored in memory is continually updated as the transducer scans and rescans an area of a patient. The resulting video data is sampled with vectors being generated and defined by X axis start point, Y axis start point, and slope. These factors are generated by potentiometers in the scan head in response to movement of the hinged arms supporting the transducer. In an X or Y vector generator, pixel data is defined only when a pixel is crossed by the vector in the X direction or the Y direction. Unfortunately, some pixels can be missed such as when the start point changes in both the X and Y direction at the same time. Consequently, the pixel at each slow axis cross over point is missed. Similarly, mixed pixels can be generated when the vector angle and start point are allowed to change at the same time.

In the compound mode of pixel generation, the stored value for a pixel cannot be reduced. Consequently, a pixel which is addressed most often has greater probability of high intensity, whereas the missed pixels are addressed less often and have a lower intensity. The lower intensity pixels form a fountain pattern or other spurious patterns which are visible in the television display.

An object of the present invention is a method of minimizing the spurious effects in an ultrasound system television display.

Another object of the invention is means for selectively updating pixel data without repetitious data updating. Briefly, in accordance with the invention an object is scanned with ultrasound transducer means, and video data is generated in response to signals from the ultrasound transducer means. Video data vectors are generated from the video data with the vectors including data intensity data for individual pixels in the system display. Pixel addresses of a vector are compared with pixel addresses of a preceding vector, and the updating of pixel intensity data is inhibited when a pixel address in the vector is present in the preceding vector.

In carrying out the invention a random access memory having storage capacity for all pixel address data in a vector is provided. A first register means sequentially receives pixel address data from the random access memory, and a first comparator means receives and compares the address data from the first register means and address data for a pixel in the succeeding vector. Pixel data update is inhibited when the comparator indicates that the address data are the same.

In a preferred embodiment three registers are serially connected whereby the address data for three consecutive pixels can be stored. Accordingly, the address data of the n pixel in the current vector can be compared with the address data for the n−1, n and n+1 pixel of the preceding vector with the pixel update disable means responding to an indentity of address data in any of the comparators.

The invention and objects and features thereof will be more readily apparent from the following detailed description and appended claims when taken with the drawing, in which:

FIG. 2 is an illustrative view of a television display in the ultrasound system of FIG. 1 and illustrating the pixel composition thereof.

FIG. 3 is an illustration of pixels into sequential vectors in the scanning system of FIG. 1.

FIG. 4 is an illustration of a fountain effect in a scanner display resulting from missed pixels.

FIG. 5 is a block diagram of circuitry in accordance with one embodiment of the present invention for minimizing spurious effects in a television display.

FIG. 6 is a detailed functional block diagram of the circuitry of FIG. 5.

Figure 1:
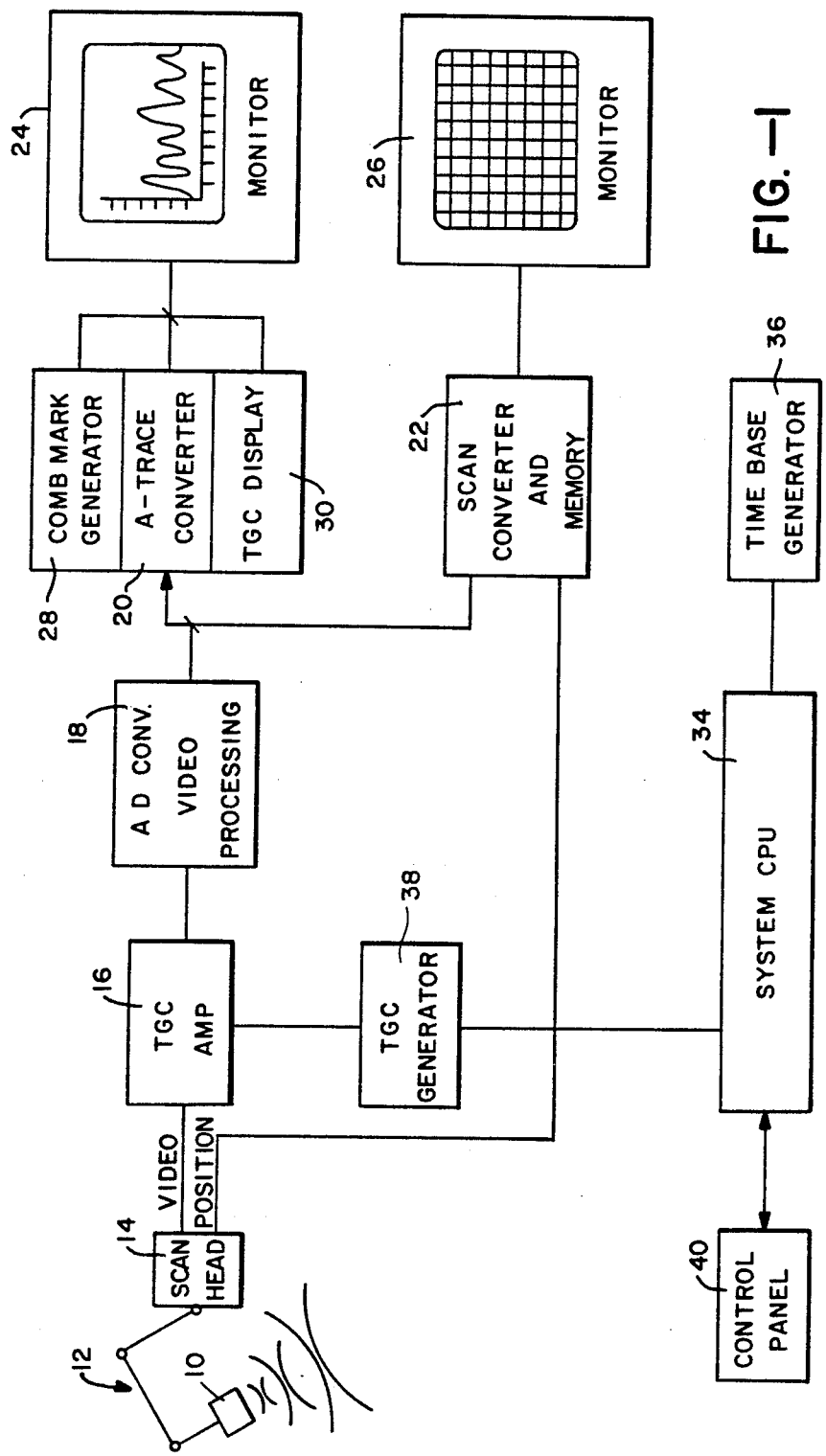
FIG. 1 is a functional block diagram of an ultrasonic scanner system.

Referring now to the drawings, FIG. 1 is a functional block diagram of an ultrasonic scanner. The system includes a transducer 10 mounted on a hinged arm system shown generally at 12 whereby transducer 10 can move freely in a single plane. Potentiometers in the scan head 14 and associated with the arms of the system generate signals indicative of the position of the scanner 10 in the plane of motion.

Scanner 10 transmits ultrasonic signals (e.g. on the order of 15 megahertz) and generates electrical signals in response to reflections of the transmitted ultrasonic signals. The generated signals are attenuated in time due to attenuation of the ultrasonic signal in passing through a patient.

The attenuated video signal is then applied to a time gain compensated amplifier 16, and the amplified signal is then applied to analog to digital conversion and video processing circuitry 18. The output of circuitry 18 is then applied to a trace converter circuitry 20 and to scan converter and memory circuitry 22 which generate the signals for controlling television monitors 24 and 26, respectively.

The A trace converter generates a signal for real time display of the amplitude of each reflected ultrasonic wave. The A trace data applied to monitor 24 identifies a horizontal position on the monitor (e.g. 525 positions)

and a vertical position defined by the raster scan of the electron beam in the monitor.

Scale markings for the display A trace are generated by comb mark generator 28, and a time gain compensation curve is provided by the generator 30.

A section view of the patient is displayed on monitor 26 in response to the scan converter and memory 22. The signal from circuitry 18 is converted to vector data in the scan converter 22 with each vector comprising a plurality of pixels for display on monitor 26. The pixel brightness data is stored in a 512×512 memory matrix with each address in the matrix accommodating a 5 bit brightness code in accordance with a 32 level Gray scale.

System control is provided by a central processing unit 34 which also drives a time base generator 36 which generates the timing signals for the system. A time gain compensation control generator 38 generates a control signal for amplifier 16, and a control panel 40 is provided for manual control of the system through the central processing unit.

FIG. 2 is an illustration of the pixels in display 26 which are arranged in 512 horizontal rows and 512 vertical columns. As the raster of the television display scans horizontally across the screen, starting at the top and progressing to the bottom of the screen, the stored brightness level for each pixel controls the intensity of the monitor electron beam thereby causing each pixel to be illuminated in accordance with the stored 5 bit code.

As described above, when the system is operating in the compound scan mode, the brightness data for each pixel is updated for each scan of the pixel with the stored pixel data being replaced if the scanned pixel data is brighter. Hence, assuming a Gaussian distribution of pixel values, the probability of producing a bright pixel is increased by scanning the pixel many times. Unfortunately, in an X or Y scan system, vectors are generated by sampling the video signal and writing a pixel only when pixels are crossed in the X direction or the Y direction. The controlling axis is determined at the start of the vector with the fastest slewing axis chosen to control the video sampling.

This sampling technique introduces the problem of missed pixels which are generated when the vector start point changes one pixel in both the X and Y direction at the same time. FIG. 3 is an illustration of two sequential vectors which produce missed pixels. Assuming an X axis and Y axis as shown with vectors generated in the direction of the arrow 44, a first vector writes data in the pixels 46 (identified by first cross hatching) with each pixel identified by an X axis crossing of the vector. The next vector comprising the pixels 48 (identified by second cross hatching) are likewise identified by X axis crossing of the vector. However, where the vectors cross the Y axis the missed pixels 50 result. Thus, the pixels 50 will be updated less often and consequently will have relatively less brightness than the written pixels. The resulting effect of the missed pixels is illustrated in the vector display of FIG. 4 in which the light pattern of the missed pixels create a fountain effect defined by the lines 52 of the lighter missed pixels.

In accordance with the present invention the spurious display effects resulting from missed pixels is minimized by preventing pixel intensity data update from sequential vectors which address the same pixel. If a particular pixel addressed in the current vector was also addressed in the previous vector, then no change in a stored pixel intensity is allowed. This is accomplished by comparing the address of the nth pixel of the current vector with the address of the nth pixel of the preceding vector, where n varies from one to the total count of pixels. Thus, if the transducer of the scanner is held stationary, the resulting video signal will not continually update the brightness of the pixels in the defined vector. Preferably, the address of the nth pixel in the present vector is compared with the addresses of the $n-1$, n, and $n+1$ pixel of the preceding vector to compensate for skewing of the addresses. Further, while the X address or the Y address of a pixel comprises 9 bits of data, only the least significant 4 bits, for example, need be compared to identify the same pixel address into sequential vectors.

FIG. 5 is a functional block diagram of one embodiment of the invention. The addresses of pixels in a vector are applied on line 60 to a random access memory 62 with the addresses of all pixels in a vector being stored in memory. With the next vector, the addresses of pixels are again applied in sequence to memory 62 and to comparators 64, 66, and 68, while the stored pixel addresses from the previous vector are sequentially read out of memory 62 and stored in register 70. The address in register 70 is transferred to register 72, and thence to register 74 in time ordered sequence. Thus, as the nth pixel address of the current vector is applied to memory 62 and to comparators 64, 66, 68, addresses for the $n+1$, n, and $n-1$ pixels of the previous vector are applied to the comparators 64, 66, 68 from the registers 70, 72, 74, respectively. Outputs from the comparator 64, 66, 68 are applied to NAND gate 76 along with the clock signal whereby an identity comparison in any one of the comparators causes NAND gate 76 to generate an output signal for disabling the display memory update for the current pixel.

Memory 62 is addressed for the read and write operations by a counter 78 which counts to the maximum storage capacity of memory 62. In a preferred embodiment, the address of the nth pixel applied as data into the memory 62 is stored in the location of the $n+1$ pixel being read from memory 62. Thus, counter 78 must be indexed by one count by counter 80 at the start of each new vector to correctly address in order the stored pixel addresses.

FIG. 6 is a detailed block diagram of the circuitry of FIG. 5 as employed in the Datason system. The reference numerals used in FIG. 5 are used for similar components in FIG. 6 with the commercial part numbers shown in parenthesis. The four least significant X address bits and the four least significant Y address bits from the scan converter are applied to the buffers (National 74LS244) shown generally at 82. Data from buffers 82 are applied to the I/O ports of 4K random access memories 62 (National 2114L-2) out of phase with the readout of stored data from memory 62 to register 70 (National 74LS373). Register 70 is serially connected with similar registers 72 and 74. As data is loaded from buffer 82 into memories 62 the data is also loaded into the comparators 64, 66, and 68 (AMD 25LS2521).

Counters 78 (National 74LS161) are driven by the Write Request Acknowledge Signals, WRA and WRA, which are generated once per pixel in the Datason system. Thus, counters 78 are indexed once per pixel and provide the sequential pixel addresses to memories 62. Since the nth pixel of the present vector is stored in the $n+1$ pixel address of the previous vector, the counters 78 are loaded and indexed by one count at the start of each new vector with the address of the first pixel provided by the counters 80. Counters 80 are indexed one count per vector by a vector start signal applied to differential amplifier 86 and through inverter 88.

The clock signal from amplifier 84 is inverted and applied through flip-flop 90. Flip-flop 90 controls the state of buffer 82 whereby the buffers are activated to load memory 62 out of phase with the reading of stored data from the memories 62. Thus, as a memory location is read, the new pixel data is written into the location.

The enable signal for comparators 64, 66 and 68 at the beginning of each new vector is controlled by a shift register 92 (National 74LS164). Shift register 92 is cleared at the start of each new vector by the signal from amplifier 86, indicating that the vector is within the monitor display area, and is clocked by the signal from amplifier 84. The CPU generated signal PSENA enables the shift register 92 only when the circuitry of FIG. 6 is to be activated. When activated, the outputs from the comparators 64, 66, 68 are applied to the NAND gate 76 which generates the Update Disable signal in response to the comparators.

In accordance with the present invention, an ultrasound scanner can be utilized in the compound mode with spurious patterns such as the fountain effect minimized by selectively disabling the pixel brightness update. While the invention has been described with reference to specific embodiments, the description is illustrative of the invention and is not to be construed as limiting the invention. Various modifications and applications may occur to those skilled in the art without departing from the true spirit and scope of the invention as defined by the appended claims.

What is claimed is:

1. A method of selectively updating pixel data for an ultrasound system display whereby spurious visual effects are minimized comprising the steps of scanning an object with ultrasound transducer means, generating video data in response to signals from said ultrasound transducer means, generating from said video data vectors including data for individual pixels in said system display, comparing pixel addresses of a vector with pixel addresses of a preceding vector, and updating pixel data when a pixel address of said vector is not present in said preceding vector.

2. The method as defined by claim 1 wherein in comparing pixel addresses the least significant bits of pixel addresses are compared.

3. The method as defined by claim 1 wherein the address information of the n−1 pixel, the n pixel, and the n+1 pixel of the preceding vector are compared with address information of the nth pixel of the current vector.

4. The method as defined by claim 1, 2, or 3 and further including the step of inhibiting pixel data update when pixel addresses are the same.

5. In an ultrasound system, apparatus for selectively updating pixel data in response to sequential vectors each including data for a plurality of pixels, comprising a random access memory, means operably connected with said random access memory for storing address information of all pixels in a vector, first means for comparing stored address information of a pixel and address information of a pixel in the succeeding vector, and means for disabling pixel data update when said address information for said stored pixel is the same as address information for the pixel in the succeeding vector.

6. Apparatus for selectively updating pixel data as defined by claim 5 and further including means for replacing stored address information for a vector with address information of the succeeding vector.

7. Apparatus for selectively updating pixel data as defined by claim 5 or 6 and further including second comparator means and third comparator means, said first comparator means, second comparator means, and third comparator means being serially connected to receive and compare the n−1, n, and n+1 pixel address information with the n pixel address information of the succeeding vector, said means for disabling pixel data update being responsive to each of said first comparator means, said second comparator means, and said third comparator means.

8. Apparatus for selectively updating pixel data as defined by claim 7 wherein said address information includes the least significant bits of a pixel address.

9. Means for selectively updating pixel data in response to sequential vectors in an ultrasound system display and the like comprising
   a random access memory having first capacity for address data for pixels in a vector,
   first register means for sequentially receiving pixel address data from said random access memory,
   first comparator means for receiving and comparing pixel address data from said first register means and pixel address data from a succeeding vector,
   means for loading said first register means and said first comparator means with pixel address data from said succeeding vector,
   means for storing said pixel address from said succeeding vector in said random access memory as previously stored address data is read from said random access memory, and
   means for inhibiting pixel data update in response to said first comparator means indicating that stored pixel address information is identical to pixel address information from said succeeding vector.

10. Means as defined by claim 9 wherein address data for a pixel of said succeeding vector is stored in said random access memory at the location of storage of the address data of the preceding pixel of the preceding vector, said means for storing said pixel address including a counter for sequentially addressing said random access memory, said counter including indexing means for indexing said counter in response to each new vector.

11. Means as defined by claim 9 or 10 and further including second register means and third register means serially connected with said first register means to receive and store then n−1, n, and n+1 pixel address information, second comparator means and third comparator means, said first comparator means, said second comparator means, and said third comparator means receiving and comparing the n+1, n, and n−1 pixel address information from said random access memory with the n pixel address information of the succeeding vector, said means for inhibiting pixel data update being responsive to each of said first, second, and third comparator means.

* * * * *